US006444170B1

United States Patent
Heid et al.

(10) Patent No.: US 6,444,170 B1
(45) Date of Patent: *Sep. 3, 2002

(54) APPARATUS FOR THE TREATMENT FOR SPECIMENS

(75) Inventors: Hans Heid, Bammental (DE); Jerome Sejournet, Grosrouvre (FR)

(73) Assignee: Microm Laborgeräte GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/274,741

(22) Filed: Mar. 23, 1999

Related U.S. Application Data

(63) Continuation-in-part of application No. 08/992,775, filed on Dec. 17, 1997, now Pat. No. 5,895,628.

(51) Int. Cl.$^7$ ............................ G01N 35/00; G01N 1/30
(52) U.S. Cl. ........................... 422/65; 422/63; 422/104; 436/43; 436/46; 118/423
(58) Field of Search .............................. 422/65, 68, 99; 141/146; 118/6, 423, 7; 23/259; 134/57

(56) References Cited

U.S. PATENT DOCUMENTS

| | | | | |
|---|---|---|---|---|
| 3,691,988 A | * | 9/1972 | Clarke | 118/6 |
| 3,837,378 A | * | 9/1974 | Kanki et al. | 141/146 |
| 3,854,440 A | * | 12/1974 | Astle | 118/7 |
| 3,903,908 A | * | 9/1975 | Logue et al. | 134/57 |
| 3,976,028 A | * | 8/1976 | Howells et al. | 118/6 |
| 4,007,011 A | * | 2/1977 | Greaves et al. | 23/259 |
| 4,363,783 A | * | 12/1982 | Sitte | 422/68 |
| 4,738,824 A | * | 4/1988 | Takeuchi | 422/63 |
| 4,834,019 A | * | 5/1989 | Gordon et al. | 118/423 |
| 5,439,649 A | * | 8/1995 | Tseung et al. | 422/99 |
| 5,573,727 A | * | 11/1996 | Keefe | 422/63 |
| 5,895,628 A | * | 4/1999 | Heid et al. | 422/65 |
| 6,080,365 A | * | 6/2000 | Thiem et al. | 422/99 |

* cited by examiner

*Primary Examiner*—Jill Warden
*Assistant Examiner*—Brian Sines

(57) ABSTRACT

An apparatus for treating cytological or histological specimens has numerous treatment stations in the form of containers, and a transport device by which the specimens to be treated are transported and deposited in the treatment stations. The transport device has a pivotable unit that can be brought under the specimens while the specimens are being transported. This pivotable unit is provided with a suction underlay on which the specimens or specimen holders are deposited, and by which treatment fluids that run out of the specimens or the specimen holders are received. Carryover of liquid residues from one treatment container to the next is thereby greatly reduced. The individual treatment containers are provided with covers, and the pivotable unit is designed to remove covers. Since the treatment containers are covered for most of the time, evaporation of the treatment liquids and release of fumes is greatly reduced.

28 Claims, 6 Drawing Sheets

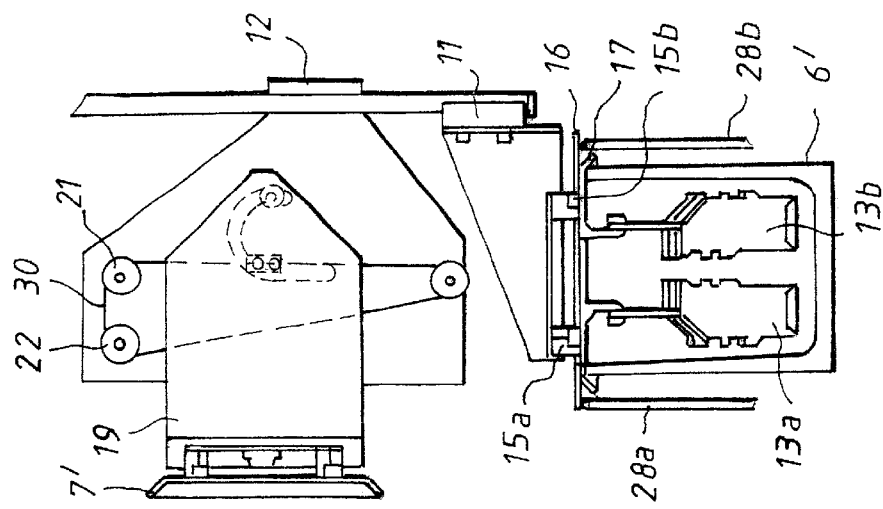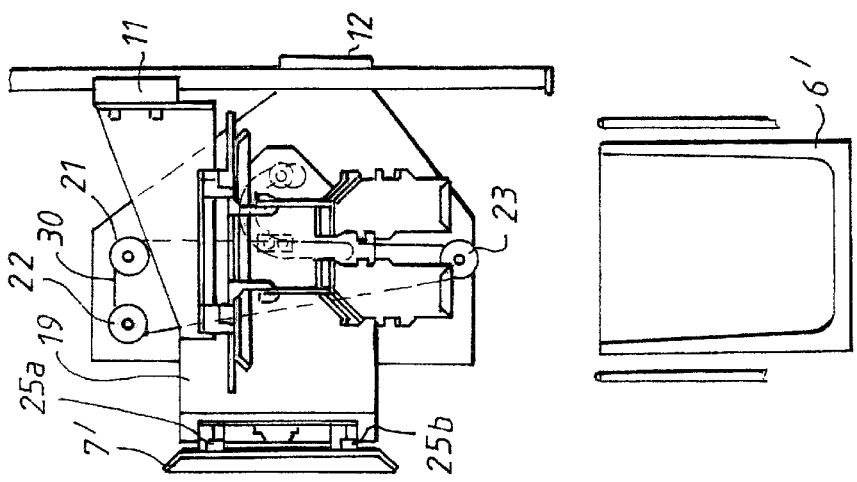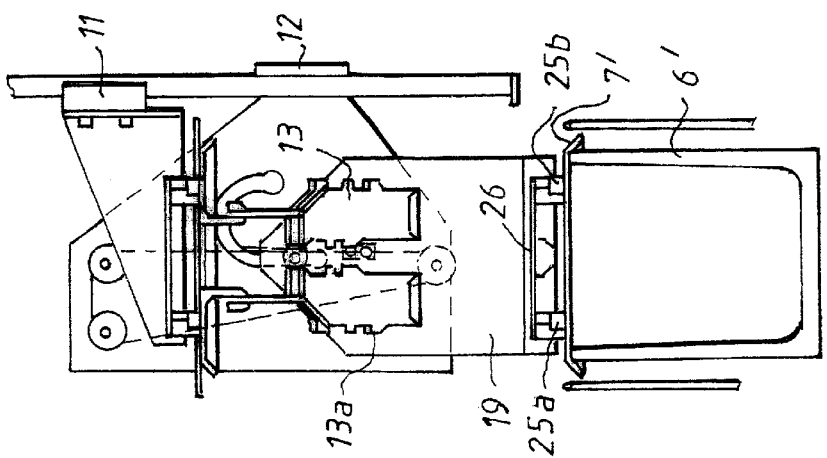

APPARATUS FOR THE TREATMENT FOR SPECIMENS

CROSS-REFERENCES TO RELATED APPLICATIONS

This application is a Continuation in Part of patent application Ser. No. 08/992,775, filed Dec. 17, 1997, of the same inventors U.S. Pat. No. 5,895,628.

STATEMENT REGARDING FEDERALLY SPONSORED RESEARCH OR DEVELOPMENT

Not applicable.

BACKGROUND OF THE INVENTION

1. Field of the Invention

This invention relates to an apparatus for treatment of specimens, and more particularly, to an apparatus for treatment of specimens with numerous treatment containers representing treatment stations. The treatment containers are set up to receive treatment solutions for the specimens. Such apparatuses are particularly used for staining histological or cytological specimens or for embedding histological or cytological specimens in an embedding medium.

2. Discussion of Relevant Prior Art

Automatic staining machines with treatment baths arranged in a 2-dimensional grid array are known, for example, from Japanese Patent JP-63-208761, European Patent EP-BL 0 586 494, WO 93/23732 and U.S. Pat. No. 4,738,824. These apparatuses have a transport device by means of which the specimens to be treated are transported from one treatment station to the next treatment station according to a program, are deposited for the prescribed treatment time in the next treatment station, and are subsequently removed. The control of the course of the program takes place completely automatically, by means of built-in processors or by means of a PC with attached keyboard and display. The treatment programs can be input and stored. The desired treatment program is subsequently selected according to requirements, called up, and automatically executed. Parallel runs of different stored treatment programs are also possible, for the most part.

To prevent health hazards due to vapor products of the solvents used (principally ethanol and xylene), a part of the known apparatuses has a hood-like equipment cover from which the solvent vapors arising in the equipment are sucked out through filters. For the most part, additional bath covers for baths or groups of baths are offered, to be placed manually on the baths or groups of baths outside the operating times, in order to prevent undesired amounts of evaporation.

A general problem with such treatment apparatuses is the prevention of the transfer of liquids from bath to bath during the course of the individual dipping processes. This is important because contamination of the baths with liquids from other baths leads to a qualitative worsening of the staining results and thus also affects the reproducibility of the results of staining. To prevent such carry-over of liquid, it is known from European Patent EP-BL 0 586 494 to provide a dripping zone between the treatment containers. The transport of the specimen or specimens between successive baths takes place along this dripping zone. However, such dripping zone tends to encumber a compact arrangement of the baths and thus to obstruct the compactness of the whole treatment apparatus, since a free space to serve as a dripping zone is required between the individual baths.

SUMMARY OF THE INVENTION

The object of the present invention is to reduce the contamination of the baths by transfer of liquid in the course of the dipping processes from bath to bath, and simultaneously to ensure a compact arrangement of the treatment containers.

Another object of the present invention is to provide a treatment apparatus with reduced amount of evaporation of the treatment solutions.

The first object is achieved by an apparatus that includes a plurality of treatment containers representing treatment stations and a transport device that transports the specimen holders in the treatment stations and between the treatment stations, deposits the specimen holders in the treatment stations and takes the specimen holders out of the treatment stations. The transport device includes a unit that is movably arranged at the transport device and comprises a suction underlay. Additionally, a computer control, which controls the movement of the transport device and of the unit, is provided which computer control causes the unit to be brought under the specimen holders and the suction underlay to contact the specimen holders after the specimen holders are taken out of the treatment containers by the transport device.

According to a preferred embodiment of the invention, the unit does not remain under the specimen holders during transport of the specimen holders to the next treatment station. Instead, the computer control causes the unit to be brought back to a transport position during transport of the specimen holders between one and another treatment station in which transport position the unit also is positioned during taking the specimen holders out of or depositing them in the treatment stations.

The second object of the invention is achieved by an apparatus that includes a plurality of treatment containers representing treatment stations and a transport device that transports specimen holders between the treatment stations, deposits the specimen holders in and takes the specimen holders out of the treatment stations. The apparatus further comprises at least one transport unit, which is designed to cover the treatment stations, and the transport device includes an engagement device that releasably engages with the transport unit.

Since the transport unit also is designed to cover the treatment stations a treatment station in which specimen holders are deposited is covered during treatment of the specimens, whereby the evaporation of the treatment solution is minimized.

The solvent residues are satisfactorily taken up by the suction underlay of the suction support by bringing the specimen holder into contact with the suction underlay. The specimen holders and the slides contained in them are held in contact with the suction support.

The unit with the suction underlay can in principle be positioned under the specimen holder either by a linear motion or by a pivoting motion. However, the provision of a pivoting motion for inserting the unit with the suction support is easier to construct.

In a further advantageous embodiment of the invention, at least some of the treatment containers are provided with removable covers. The unit that can be positioned under the specimen holders during transport also has a device, on the side remote from the suction support, for removing the cover. Then the cover can be taken off the container concerned before a specimen holder is put in place, and can be set down on the container of the preceding treatment station or on the container from which another specimen holder next has to be taken out, after the specimen holder has been set down.

Furthermore, transport units, that are preferably also separable from the transport device, and on which the specimen holders are received, are constructed for covering the treatment containers. This ensures that the treatment containers are nearly always covered, and that only one transport container is open during the very short transfer time of the transport mechanism from one treatment container to the next. Since the transport containers are nearly always covered, evaporation is greatly reduced in comparison with equipment in which vapors emerging from uncovered containers are sucked out and the evaporation of the solvent is exacerbated by the suction. The consumption of solvent and likewise endangering health and the environment are thereby reduced.

In a preferred embodiment of the invention, the transport device has a vertical guide on which a slider is received, with a device to receive the specimen holder or the transport unit. A carrier for the unit that is to be brought under the specimen holder is also attached to the same vertical guide. The unit that is to be brought under the specimen holder is received on this carrier in such a manner that it can execute a combination of a linear vertical motion and a pivoting motion about a horizontal axis. The motion of the slide and of the unit that can be brought under the specimen holder are controllable independently of each other. Thus only a common horizontal guide is required for handling the specimens or specimen holders and handling the cover.

Magnets, preferably electromagnets, can be provided on the transport device for removing the cover and/or for releasably removing the specimen holder. When permanent magnets are used, an additional mechanism is also required for turning the magnetic force on and off, for example by turning the permanent magnets, or for example by applying a force that is greater than the magnetic force.

Like the automatic staining systems known from the documents mentioned previously, the apparatus according to the invention also has a computer control for automatically running stored and selected programs, by means of which the specimen holders are automatically transported by the transport device to the individual treatment stations that are provided according to the program; deposited in the treatment stations for the residence time according to the program; removed after the programmed residence time has elapsed; and transported to the next treatment station according to the program. Furthermore, the computer control effects lifting the associated cover by means of the transport device when a new treatment station is reached according to the program, and after the specimen holder has been set down in the new treatment station, the cover taken from the new treatment station is deposited on the previous treatment station according to the program. After a specimen holder is taken out of the treatment station, the computer control furthermore causes a unit to be automatically brought under the specimen holder. Subsequently, by a relative motion between the specimen holder and the unit that can be brought under the specimen holder, the specimen holder is deposited on the unit. The computer control can be set up for the simultaneous, parallel course of different and/or like treatment programs.

BRIEF DESCRIPTION OF THE DRAWINGS

The invention will now be described in greater detail, taken together with the drawings, in which:

FIGS. 4a–h show sequences in the course of operation during transport of slide holders from one treatment station to the succeeding one; and FIG. 5 shows a block circuit diagram for a process control according to the invention.

DETAILED DESCRIPTION OF PREFERRED EMBODIMENTS

Figure 1:
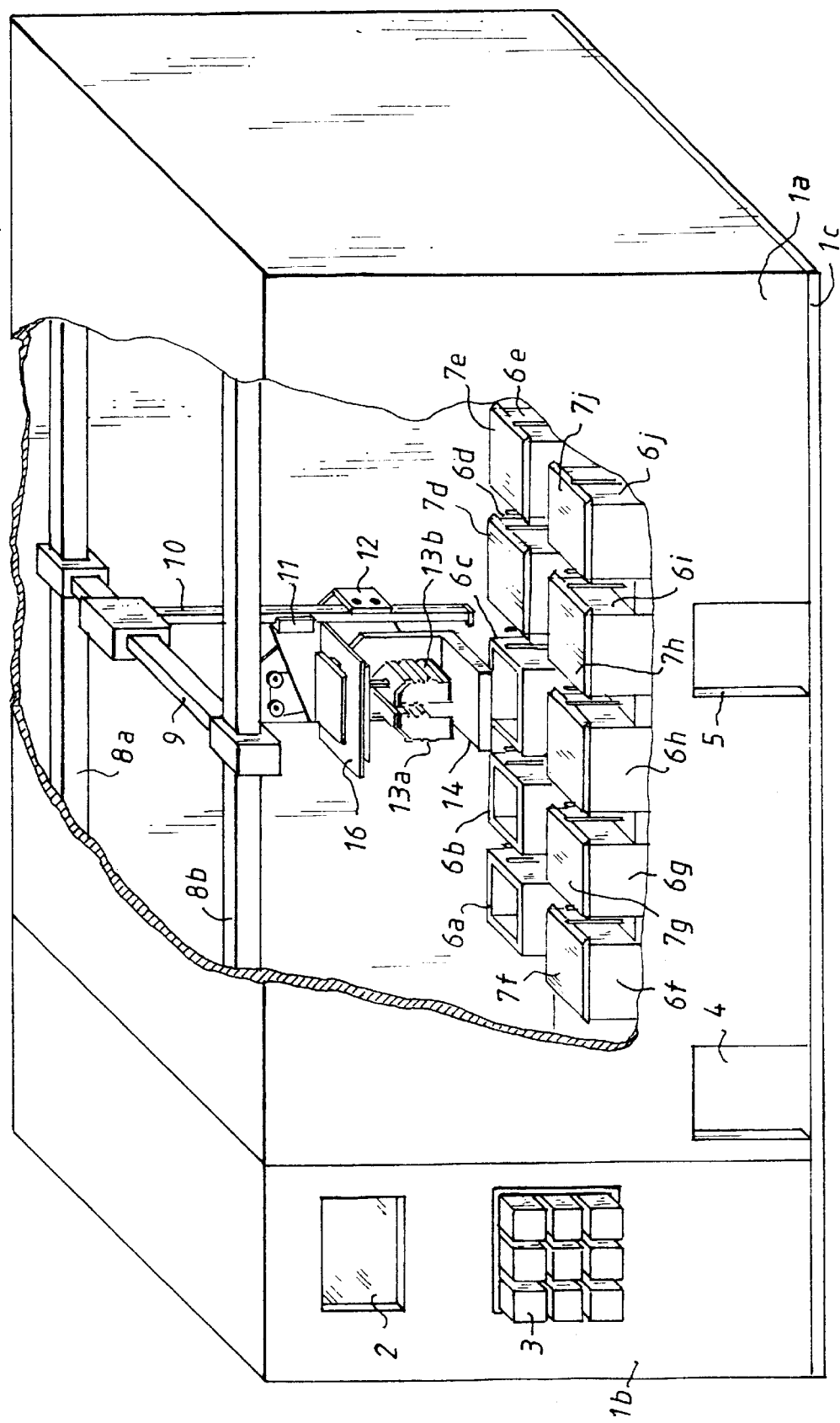
FIG. 1 shows a view of the apparatus according to the invention, in partial elevation.

The apparatus according to the invention is shown by FIG. 1, exemplified by an automatic staining system (1). The automatic staining system (1) includes a fixed housing part (1b) that is fixedly mounted on a baseplate and a housing part (1a) that is removable from the baseplate. The processor (31) and the memory (32) (see FIG. 5) for controlling or for storing a large number of staining programs is arranged in the fixed housing part (1b). A display field (2) and a keyboard (3) are arranged at the front side of the fixed housing part (1b). The keyboard is used for the input of staining programs to be stored and for calling up stored staining programs. The respective input data or likewise, program comments when calling up stored programs, are shown on the display (2).

The removable housing part (1a) has two openings (4, 5) that act as loading or unloading stations. A basket suspension with specimen holder baskets is inserted into the loading station and acts as a transport unit and, after the staining program to be executed has been called up or input, is taken up, respectively transported to the treatment station according to the program, and is set down in the removal station (5) after the complete staining program has been carried out. The treatment stations are embodied as treatment containers (6a–6j), intended to receive treatment solutions, arranged in a 2-dimensional grid array on the baseplate. Most of the treatment containers (6c–6j) are covered by means of covers (7c–7j). Only treatment containers that represent washing stations, and consequently are filled only with water, are uncovered. If required, covers (7c–7j) can be taken from other treatment stations and deposited on these washing stations.

Two horizontally directed linear guides (8a, 8b) for the transport device are provided in the upper region, and are thus above the treatment containers (6a–6j). The linear guides are received via supports on the baseplate (1c). A horizontally movable crossbar (9) is guided on the linear guides (8a, 8b), is movable horizontally along these linear guides (8a, 8b), and is driven by means of drive motors (not shown) in the crossbar (9). A vertical guide (10) is received on the crossbar (9), on which it is horizontally movable in a direction at right angles to the direction of movement of the crossbar. A vertically movable slider (11) is received on this vertical guide (10). The specimen holder baskets (13a, 13b) with the specimens to be stained are received on this vertical slider (11). A unit (14) is furthermore attached to the vertical guide with a fastening clamp (12), and a portion (19) of the unit (14) can be pivoted to come under the specimen holder baskets (13a, 13b) when these are lifted out of the treatment containers. The detailed construction of the vertical slider (11) with the components received thereon and of the unit (14) is described in further detail below, with reference to FIGS. 2 and 3.

The whole transport device has a crane-like structure. The movement of the transport device takes place under computer control by the control processor (31) (see FIG. 5) provided in the fixed housing part (1b), according to the called-up or input staining program. The transport device has a total of four drives (37–40), that are controlled by the processor (31) via four interface cards (33–36). Three drives (37–39) for the movement of the crossbar (9) along the horizontal guide (8a, 8b), the movement of the vertical guide (10) relative to the crossbar, and the movement of the slider (11) along the vertical guide (10) have encoders, whose signals are fed back to the processor via the interface cards (33–35), so that the exact position of the transport device is precisely known at any point in time. The remaining drive (40) is for the movement of the unit that is pivotable under the specimen holder baskets (13). This drive (40) is described in more detail hereinbelow, and has three microswitches (not shown). On reaching the microswitches, the drive (40) is stopped, and a signal characterizing the present stopping position is emitted to the processor (31). Furthermore, the positions of the treatment containers (6a–6j) are known. The processor control is designed as disclosed, for example, in Japanese Patent JP 63-208761, such that different staining programs can be executed simultaneously, in that the transport device, after depositing the specimen holder baskets (13a, 13b) in a treatment container, transports other specimen holder baskets within the apparatus during the treatment time.

Corresponding algorithms to effect processor control that have a parallel course of several staining programs are known from the aforementioned Japanese Patent, and are therefore not further described here.

The treatment containers (6a–6n), with the exception of the washing stations (6a, 6b), are normally covered with covers (7c–7n) and, as further described hereinbelow, the specimen holder baskets (13a, 13b) are also arranged on a transport unit that is constructed like a cover. Thus, the treatment containers are covered even during the immersion of the specimen holder baskets (13a, 13b), and hardly any solvent vapors of the treatment solutions escape from the present apparatus. Evacuation of air from the removable housing part (1a) is therefore not necessary. However, evacuation can also be suitable when solvents are used that are particularly dangerous to health, or which have a particularly intense odor.

Figure 2:
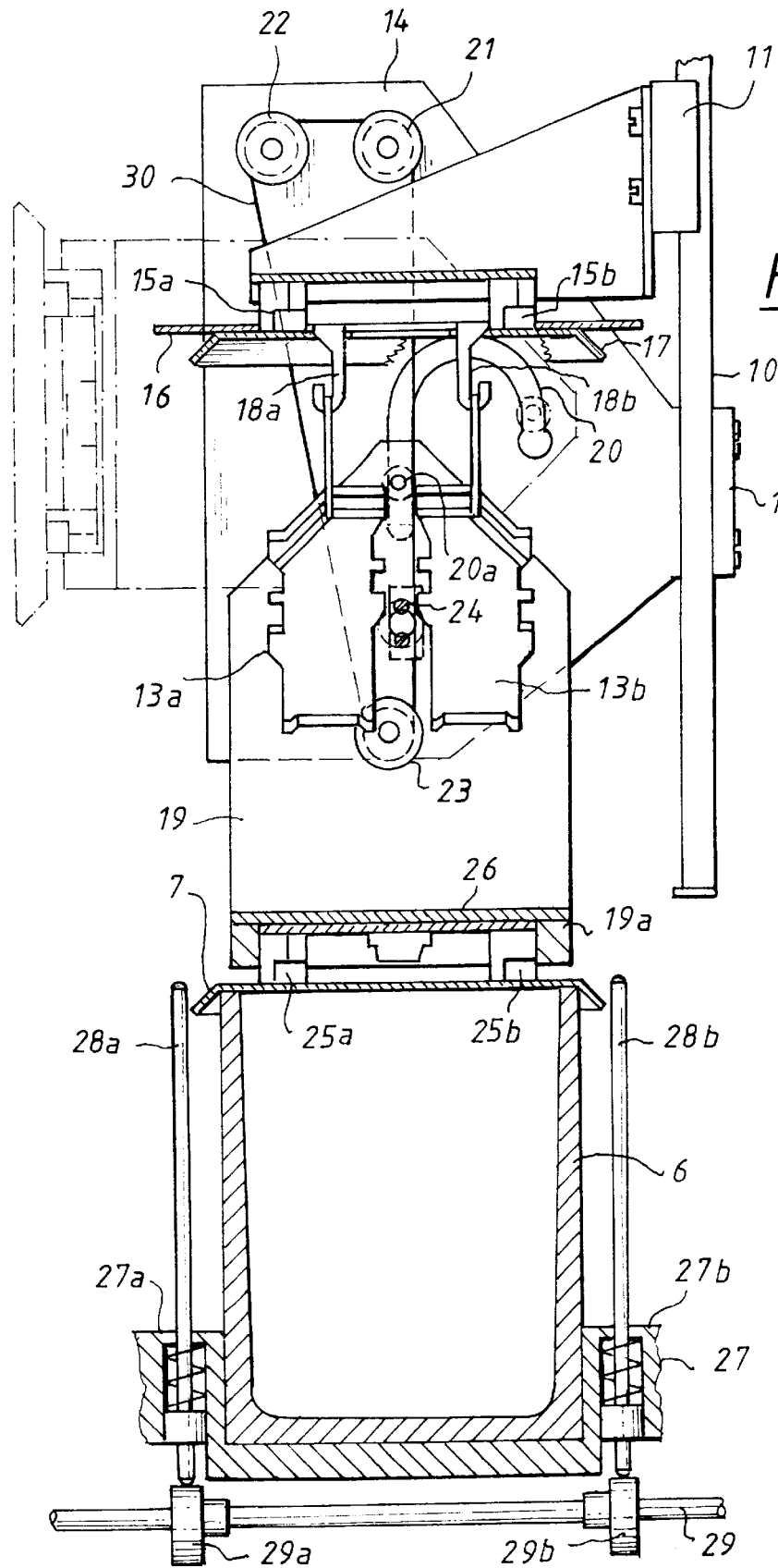
FIG. 2 shows a vertical section through the transport unit of the apparatus according to the invention.
Figure 3:
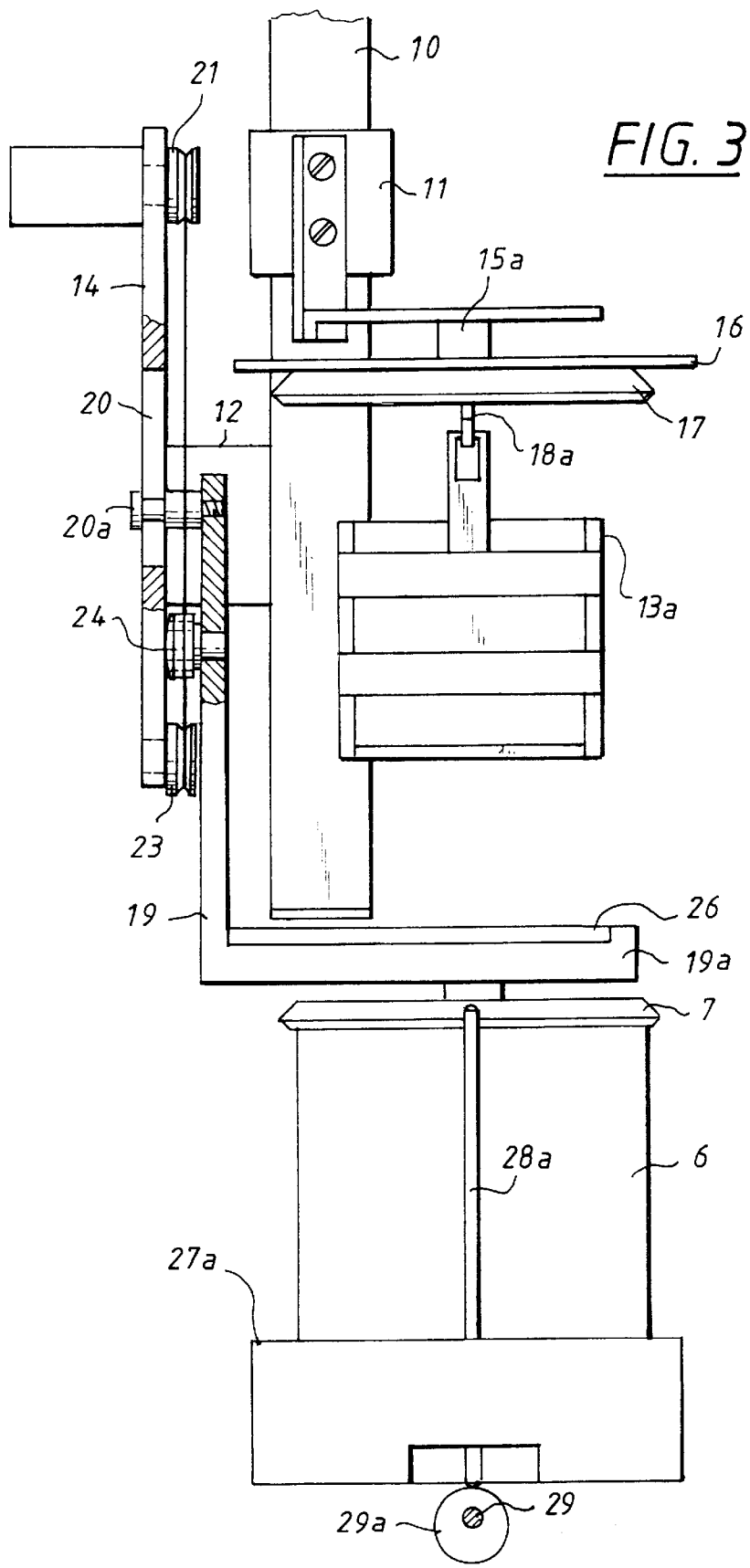
FIG. 3 shows a vertical section through the transport unit in a plane at right angles to FIG.

As can be gathered from the two enlarged sectional views of FIGS. 2 and 3, a vertical slider (11) is guided on the vertical guide (10), and two electromagnets (15a, 15b) are provided on the vertical slider (11) by means of an angular carrier. The electromagnets (15a, 15b) releasably engage the slide transport units, several of which are as a rule supplied with the equipment. This slide transport unit has a cover plate (16) on which hooks (18a, 18b) are arranged for the suspension of the slide baskets (13a, 13b). Furthermore, the slide transport units have a cover-shaped part (17) that is identical to the covers (7) of the treatment containers (6). This cover-shaped part (17) has two holes, through which the hooks (18a, 18b) are passed. At the same time, the cover plate (16) has two holes, through which the magnets (15a, 15b) of the vertical slider (11) can be guided onto the cover-shaped part (17). By raising the slider (11), the cover plate (16) which rests on the cover-shaped part (17), the hooks (18a, 18b) attached to the cover plate, and the slide baskets (13a, 13b) received on them, are all likewise raised. This construction of the transport unit serves to move the slide baskets (13a, 13b) into closed treatment containers (6), as further described hereinbelow. The slide baskets (13a, 13b) are constructed for insertion of many slides, and have a ribbed external structure, so that the treatment solution can come into contact with the slides contained in the slide baskets (13a, 13b), and with the specimens located on the slides.

A carrier plate (14) is received on the vertical guide (10) by means of a fastening clamp (12), and is arranged substantially beneath the plane of the drawing in FIG. 2. The carrier plate (14) has a curved, milled-out portion (20), in which an angular plate (19) is received by means of a guide pin (20a). Furthermore, a belt drive is provided on the carrier plate (14) and is guided by three rollers (21, 22, 23), the guide cable (30) of which is attached by means of a rotatable clamp (24) to the angular plate (19). One of the three rollers (21) is motor-driven (drive 4 in FIG. 5). When the drive roller (21) turns to the left, the clamp (24) is pulled upwards, and the guide pin (20a) slides along the milled-out portion (20), with the result that the angular plate (19) is first pulled upward and, because of the arcuate shape of the milled-out portion (20), is subsequently pivoted into the position which is shown dot-dashed.

An open-pore, foam-like, suction underlay (26) lies on top of the angled portion (19a) of the angular plate (19), on the side facing the slide baskets (13a, 13b). This suction underlay (26) is removable and interchangeable, and serves to receive treatment solutions that run out of the slide baskets (13a, 13b). If necessary, the support for the suction underlay can be constructed in a trough shape, in order to prevent liquid running out when the angular plate (19) is pivoted. Four additional electromagnets (25a, 25b) are provided on the side of the angled portion (19a) of the angular plate (19) remote from the suction underlay (26), only two being shown in FIGS. 2 and 3. These electromagnets (25a, 25b) serve to remove the cover (7) from the treatment containers (6).

When traveling to a new treatment station, the treatment container (6) of which is still covered, the angular plate (19) of the pivoting part is first lowered to the right, by rotation of the drive roller (21), until the magnets ($^{25}$a, 25b) are deposited from above on the cover (7) of the treatment container (6). In this lowered position, the first of the three microswitches (mentioned above) of the drive responds. The magnets (25a, 25b) are then switched on, and the cover (7) is lifted by means of the angular plate (19), by rotation of the drive roller (21) to the left, and is then pivoted into the position drawn dot-dashed in FIG. 2. The movement travels over the response of a second microswitch of the drive 4, until the third microswitch responds that indicates the pivoted position, shown dot-dashed, of the angular plate (19). After the dot-dashed, pivoted position has been reached, the slider (11) with the slide baskets (13a, 13b) held on it travels vertically downward until the cover-shaped portion (17) of the transport unit lies against the treatment container and covers the treatment container. The magnets (15a, 15b) for holding the transport unit are then released, and the transport device is separated from the transport unit. The slider (11) thereafter again travels further upward vertically, and the transport device also travels to the position of the previous treatment station, in order to deposit, on the treatment container of the previous treatment station, the cover that is carried on the angular plate (19) of the transport device.

When the transport unit rests with the cover-shaped portion (17) on the treatment container (6), the edges of the cover plate (16) that project beyond the cover-shaped portion (17) come into contact with push rods (28a, 28b) that are arranged in the apparatus floor and are set in rising and falling motion by means of a shaft (29) with eccentrics (29a, 29*b*), which runs in the device floor. The movements of the push rods (28*a*, 28*b*) are transmitted to the cover plate (16) and hence to the slide baskets (13*a*, 13*b*) suspended on the cover plate, so that the slide baskets (13*a*, 13*b*), with the lid portion (17) fixedly resting on the treatment container, likewise execute the rising and falling movement. A relative movement is thus brought about between the slide baskets (13*a*, 13*b*) and the treatment solution. The floor structure of the apparatus is denoted by (27), and elevations of the floor structure, by which the position of the treatment containers (6) is established, are denoted by (27*a*, 27*b*).

To take the slide baskets (13*a*, 13*b*) out of one treatment station (5) and for the transportation of these slide baskets to the next treatment station, the transport device again travels to the position of the treatment container (6). The vertical slider (11) is thereby lowered, until the magnets (15*a*, 15*b*) arranged on the vertical slider (11) come into contact with the cover-shaped portion (17) of the transport unit through the holes of the cover plate (16). The electromagnets (15*a*, 15*b*) are subsequently switched on again, and the transport unit, together with the baskets (13*a*, 13*b*) suspended on the cover plate (16) are raised out of the treatment container (6). The pivoting unit (19) is then pivoted further downward by turning the drive roller (21) to the right, so that the suction underlay (26) is pivoted in, between the slide baskets (13*a*, 13*b*) and the treatment container (6). This position is detected by the second microswitch, and when it responds, the turning of the drive roller (21) to the right is stopped.

In a following step, the slider (11) with the slide baskets (13*a*, 13*b*) is caused to travel vertically downward far enough for the suction underlay (26) to come into contact with the lower edge of the slide baskets (13*a*, 13*b*).

Residues of liquid that run out of the slide baskets are received by the suction underlay (26), by the contact between the suction underlay (26) and the slide baskets (13*a*, 13*b*). The foam-like suction underlay (26) is simultaneously deformed and, due to the step-like structure of the slide baskets (13*a*, 13*b*), partially penetrates into the slide baskets (13*a*, 13*b*) from below, thereby coming in contact with the slides received in the slide baskets. The slides are thus fixed.

Afterwards the slider (11) is lifted again to its original position and the pivoting unit (19) is moved up again into its original position (2), as indicated by the dash-dotted lines, by a reverse rotation of the drive roller (21).

By movement of the vertical guide (10) and the crossbar (9) (see FIG. 1) along the horizontal guides (8*a*, 8*b*), travel now takes place to the next treatment station position according to the program. The shortest combination of distances to the next treatment station is chosen as the travel path. Travel along defined paths is not required. Since the slides are fixed by the suction underlay, the slides are not caused to vibrate during transportation. Thus, little noise is generated.

Figure 4C:
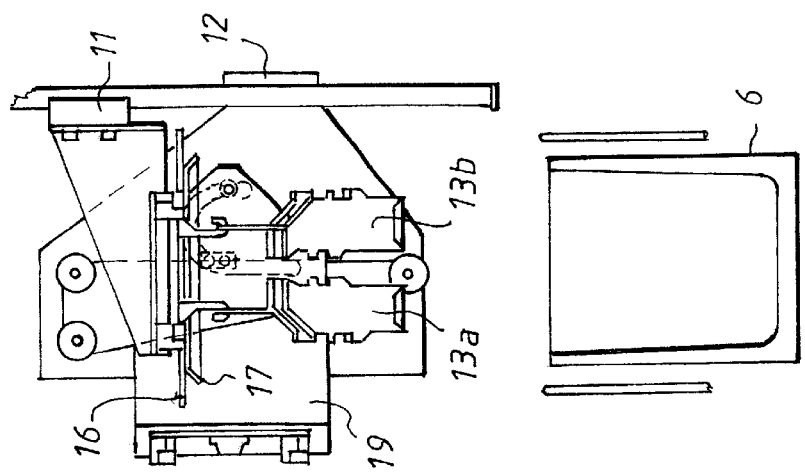
Figure 4B:
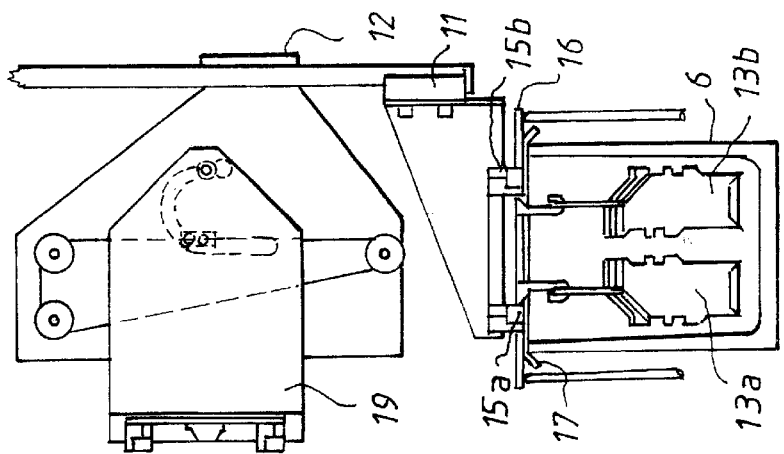
Figure 4A:
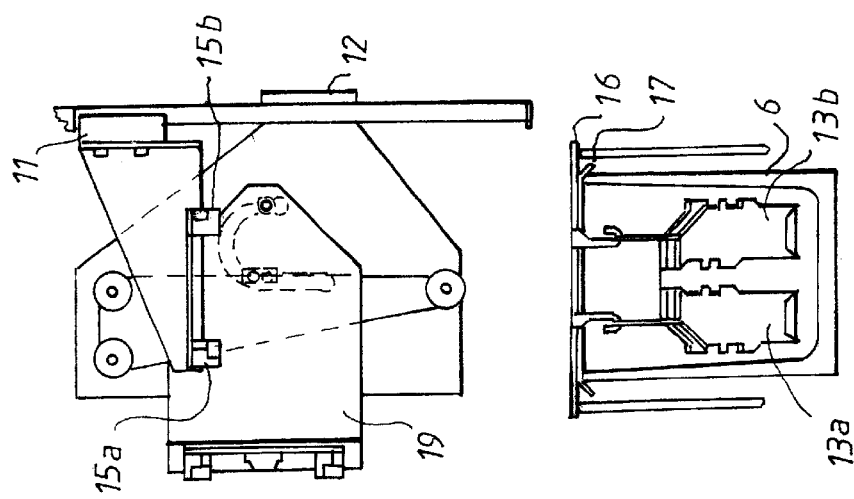
Figure 4E:
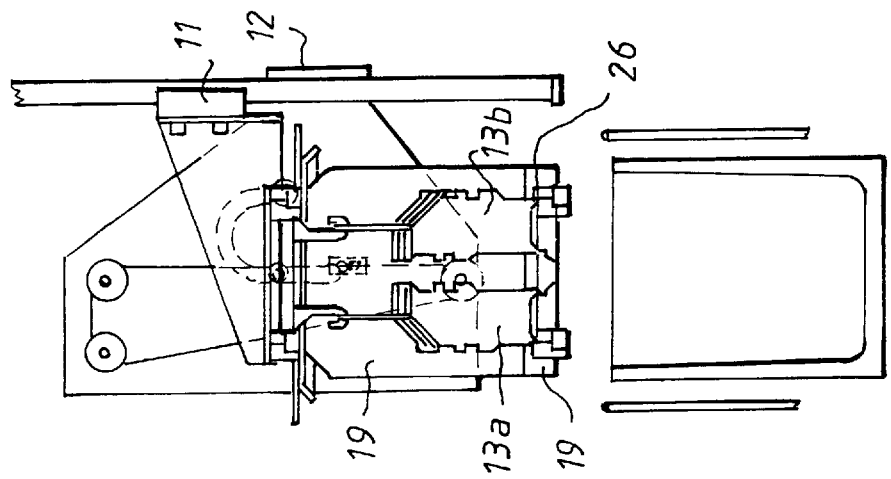
Figure 4D:
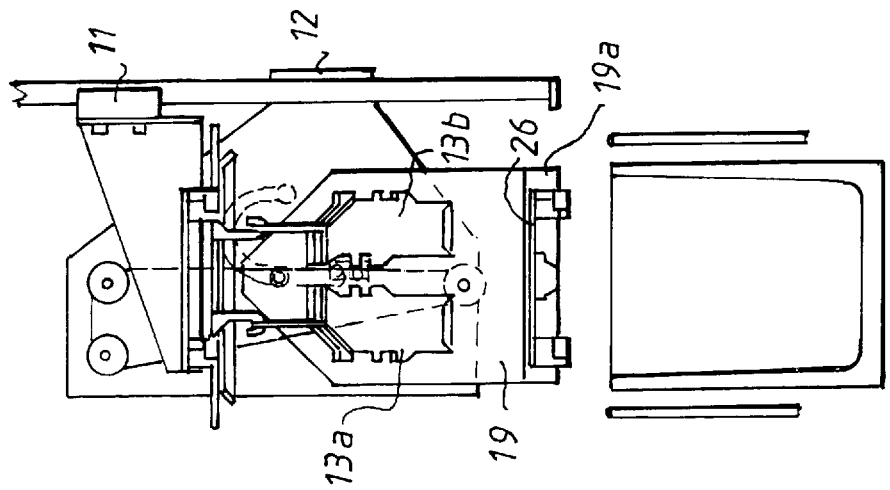

After the next treatment station has been reached, the process described above begins anew. That is, the angular plate (19) is lowered by a further turning of the drive roller (21) to the right until the first microswitch responds. The cover of the treatment container is removed by the pivoting unit (19), and subsequently the transport unit is set in the new treatment container by travel of the slider (11). The whole course of functioning is described once again hereinbelow with reference to FIGS. 4*a*–4*h*:

In FIG. 4*a*, the slide baskets (13*a*, 13*b*) suspended on the transport unit (16, 17) are located in a treatment station, and it is assumed that the treatment time for this treatment station according to the program has expired. The slider (11) is then lowered, so that the magnets (15*a*, 15*b*) of the slider (11) come into contact with the cover-shaped part (17) of the transport unit (FIG. 4*b*). After the electromagnets (15*a*, 15*b*) on the slider (11) have been switched on, the slider (11) is displaced vertically upward and the slide baskets (13*a*, 13*b*) are thus lifted out of the treatment container (FIG. 4*c*). The pivoting of the pivoting unit (19) now takes place, whereby the suction underlay (26) is pivoted in between the slide baskets (13*a*, 13*b*) and the treatment container (FIG. 4*d*). The slider (11) is then caused to travel downward along the vertical guide (10) until the suction underlay (26) comes into contact with the floor surface of the slide baskets (13*a*, 13*b*) (FIG. 4*e*). Afterwards, the slider (11) is lifted again (FIG. 4*d*) and the pivoting unit (19) is moved up again into its original position (FIG. 4*c*). When the next treatment station (6') is reached, the pivoting unit (19) is lowered (FIG. 4*f*) until the magnets (25*a*, 25*b*) reach the cover (7') of the treatment station. After the electromagnets (25*a*, 25*b*) are switched on, the cover (7') is raised by means of the cable drive (30, 21, 22, 23) and is pivoted sideways (FIG. 4*g*). Thereafter the slider (11) is lowered until the cover-shaped part (17) rests on the treatment container (61) of the treatment station (FIG. 4*h*) and the magnets (15*a*, 15*b*) on the slider (11) are released. The transport unit (16, 17) with the slide baskets (13*a*, 13*b*) suspended in it is thereby separated from the slider (11), and the slider (11) is again caused to travel upward. Due to the rising and falling movement of the push rods (28*a*, 28*b*), the cover plate (16) now likewise executes the rising and falling movement of the push rods during the treatment time, so that there results a relative movement between the treatment liquid and the slide baskets and the slides contained in them.

After raising the slider (11), the transport device can either travel to another treatment station in order to take out a slide basket inserted there or can move to a washing station to deposit the cover (7') still carried by the unit (19) there. In the first case the transport device takes out the slide basket and afterwards deposits by a respective movement of the unit (19) the still carried cover (7'). The second case only applies if a new slide basket has to be picked up in the loading station and transported to its first treatment station. In any other cases long time consuming movements of the transport device just for taking the picked up cover are avoided. The decision as to which of the alternatives is selected is effected by the process control which, when several programs are running in parallel, produces an overall program by selection of the starting time and/or by variation of the treatment times within permissible limits, thus ensuring an undisturbed parallel course of several programs.

As can be seen from the course of functioning described with reference to FIGS. 4*a*–4*h*, three defined end positions are provided for the pivoting unit (19), and are respectively defined by the response of one of the three microswitches. These three end positions are the sideways pivoted position shown in FIGS. 4*a*–4*c*, 4*g* and 4*h*; the position with the suction underlay (26) aligned horizontally, shown in FIGS. 4*d* and 4*e*; and the lowered position of the pivoting unit (19) for removing or depositing a cover, shown in FIGS. 4*f*.

It can be advantageous to provide a shaking movement to the specimen holders after taking them out of a treatment station and before that unit (19) with the suction underlay contacts the specimen holders. By such shaking movement the dripping off of the treatment solution is further improved. For generating such shaking movement the computer control can switch on and off the drives of the transport device to move back and forth as well as up and down, but with a sufficient high frequency so that during the periods in which the drives are switched on only very short movements of distances of only a few millimeters occur.

In a further embodiment of the invention, yet another emptying program can be provided, by means of which treatment solutions that have become unusable are automatically sucked out. A further, specially constructed cover can be provided for this purpose. It has a suction tube that reaches to the floor of the treatment containers, and is connected to a suction pump. This additional cover is normally deposited in a special parking position, and when required can be taken up by the magnets (15a, 15b) of the slider (11) in this parking position and caused to travel to the treatment station to be emptied. After removal of the cover that covers the treatment station concerned, by means of the pivoting unit, this special aspiration cover is placed on the treatment station, and the treatment solution is sucked out by switching on the pump. During the aspiration process, other slide baskets can be caused to travel within the apparatus in the manner described hereinabove, so that the aspiration of a treatment solution can be completely integrated into the normal operation of the equipment.

The invention has been described using the example of an automatic staining machine, with reference to the preferred embodiment shown in the Figures. However, the invention can also be used for other automatic treatment machines for histological or cytological preparations, and particularly in so-called tissue processors, which are used for embedding a preparation in an embedding medium.

What is claimed is:

1. An apparatus for treatment of specimens, comprising:
   a plurality of treatment containers representing treatment stations,
   a transport device that transports a specimen holder between the treatment stations, deposits said specimen holder in and takes said specimen holder out of said treatment stations,
   a unit movably arranged at said transport device, said unit comprising a suction underlay that is brought under said specimen holder to be contacted by said specimen holder, and
   a computer control controlling movement of said transport device and of said unit, said computer control causing said unit to be brought under said specimen holder and said specimen holder to contact said suction underlay after taking said specimen holder out of a treatment station.

2. The apparatus of claim 1, wherein said unit has a transport position in which said unit is positioned during taking said specimen holder out of said treatment station and wherein said computer control further causes said unit to be brought back to said transport position during transport of said specimen holder between one and another treatment station.

3. The apparatus of claim 1, wherein said unit is pivotably arranged on said transport device.

4. The apparatus of claim 1, wherein said transport device comprises a receiving device that takes up specimen holders, a vertical guide on which said receiving device and said unit are vertically movably guided independently of each other.

5. The apparatus of claim 1, wherein at least a portion of said treatment stations are provided with removable covers, and said unit has, on a side remote form said suction underlay, a removal device by which said covers are removed.

6. The apparatus of claim 1, further comprising at least one transport unit for said specimen holders, wherein said transport device includes a engagement device that can releasably engage with said transport unit, and said transport unit is designed to cover said treatment stations.

7. The apparatus of claim 5, wherein at least one of said removal device and said engagement device comprise magnets.

8. The apparatus of claim 7, wherein said magnets comprise electromagnets.

9. The apparatus of claim 1, further comprising a computer control for automatically running stored and selected treatment programs, wherein said specimen holders are automatically transported device to said individual treatment stations according to a selected program, are deposited in said treatment stations for programmed residence time, and are taken out after expiration of said programmed residence time and transported to a new treatment station according to a selected program.

10. The apparatus of claim 2, wherein after said specimen holder is taken out of said treatment station, said computer control controls a removal device to close said treatment station with a cover taken at said removal device during approaching said treatment station.

11. The apparatus of claim 10, wherein said computer control is designed for simultaneous, parallel running of different of like treatment programs.

12. The apparatus of claim 11, wherein said treatment stations are arranged in a two-dimensional grid array, and said transport device is designed to move in three mutually perpendicular directions.

13. An apparatus for treatment of specimens, comprising:
    a plurality of treatment containers representing treatment stations,
    at least one transport unit for specimen holders, and
    a transport device,
    wherein said transport device includes an engagement device that releasably engage s with said transport unit,
    wherein said transport device is designed to transport said transport unit between said treatment stations, and
    wherein said transport unit is designed to cover said treatment stations.

14. The apparatus of claim 13, wherein said transport unit comprises a cover plate and said apparatus further comprises push rods performing rising and falling movements, said push rods coacting with said cover plate causing an up and down movement of said transport unit when deposited in said treatment station.

15. The apparatus of claim 14, wherein said transport unit additionally comprises a cover shaped part having at least one hole, and said specimen holders are mounted to said cover plate through said at least one hole of said cover shaped part.

16. The apparatus of claim 2, wherein said unit is positioned under said specimen in said transport position and said unit is not positioned under said specimen holder in said treatment position.

17. An apparatus for treatment of specimens, comprising:
    a plurality of treatment containers representing treatment stations,
    a transport device that transports a specimen holder between the treatment stations,
    deposits said specimen holder in and takes said specimen holder out of said treatment stations,
    a unit movably arranged at said transport device, said unit comprising a suction underlay that is brought under said specimen holder to be contacted by said specimen holder, and said suction underlay comprising an opened pore or foam material, a computer control controlling movement of said transport device and of said unit, said computer control causing said unit to be brought under said specimen holder and said specimen holder to contact said suction underlay after taking said specimen holder out of a treatment station.

18. The apparatus of claim 17, wherein said unit has a transport position in which said unit is positioned during taking said specimen holder out of said treatment station and wherein said computer control further causes said unit to be brought back to said transport position during transport of said specimen holder between one and another treatment station.

19. The apparatus of claim 17, wherein said unit is pivotably arranged on said transport device.

20. The apparatus of claim 17, wherein said transport device comprises a receiving device that takes up specimen holders, a vertical guide on which said receiving device and said unit are vertically movably guided independently of each other.

21. The apparatus of claim 17, wherein at least a portion of said treatment stations are provided with removable covers, and said unit has, on a side remote form said suction underlay, a removal device by which said covers are removed.

22. The apparatus of claim 21, further comprising at least one transport unit for said specimen holders, wherein said transport device includes a engagement device that can releasably engage with said transport unit, and said transport unit is designed to cover said treatment stations.

23. The apparatus of claim 22, wherein at least one of said removal device and said engagement device comprise magnets.

24. The apparatus of claim 23, wherein said magnets comprise electromagnets.

25. The apparatus of claim 17, further comprising a computer control for automatically running stored and selected treatment programs, wherein said specimen holders are automatically transported device to said individual treatment stations according to a selected program, are deposited in said treatment stations for programmed residence time, and are taken out after expiration of said programmed residence time and transported to a new treatment station according to a selected program.

26. The apparatus of claim 25, wherein after said specimen holder is taken out of said treatment station, said computer control controls a removal device to close said treatment station with a cover taken at said removal device during approaching said treatment station.

27. The apparatus of claim 25, wherein said computer control is designed for simultaneous, parallel running of different of like treatment programs.

28. The apparatus of claim 17, wherein said treatment stations are arranged in a two-dimensional grid array, and said transport device is designed to move in three mutually perpendicular directions.

* * * * *